United States Patent

Ozkan

[19]

[11] Patent Number: 4,681,782
[45] Date of Patent: Jul. 21, 1987

[54] ARTICLE FOR DETERMINING THE PRESENCE OF IMMUNE COMPLEXES

[75] Inventor: Adil N. Ozkan, Salt Lake City, Utah

[73] Assignee: Biostar Medical Products, Inc., Boulder, Colo.

[21] Appl. No.: 538,493

[22] Filed: Oct. 3, 1983

Related U.S. Application Data

[63] Continuation-in-part of Ser. No. 363,967, Mar. 31, 1982, Pat. No. 4,450,231.

[51] Int. Cl.[4] .................. G01N 33/536; G01N 33/539
[52] U.S. Cl. ...................................... 428/36; 428/173; 428/411.1; 428/507; 428/518; 428/520; 428/532; 435/7; 435/293; 436/507; 436/529; 436/531; 436/538; 436/539; 436/807; 436/809
[58] Field of Search .................... 435/7, 293; 436/506, 436/538, 539, 821, 507, 529, 531, 809; 428/173, 520, 518, 507, 532, 411.1, 36

[56] References Cited

U.S. PATENT DOCUMENTS 4,246,319 1/1981 Jacobone .......................... 428/520
4,450,231 5/1984 Ozkan ................................ 435/7

Primary Examiner—Sidney Marantz
Attorney, Agent, or Firm—Jerry W. Berkstresser

[57] ABSTRACT

An immunoassay of a specimen of a serum or the like to determine the composition of immune complexes, includes producing on a plastic base a layer of a non-proteinaceous, non-ionic polymer which will adhere to the plastic base and has the capability of adsorbing immune complexes of the specimen, placing a specimen on the layer and treating the layer to produce an indication of the composition of the immune complexes. The polymer may be polyethylene glycol, dextran, polyvinyl chloride, a polymeric polyol or an adduct of polyethylene glycol or mixtures thereof. Washing with conventional solutions, addition of monoclonal and/or polyclonal antibodies coupled with an enzyme and addition of a substrate reactive therewith to determine the antigen component, are similar to the ELISA test, with color measurement as by spectrophotometer. Or, the addition of anti IgG-I[125] and measurement by a scintillation counter may be used. Addition of IgG, IgA, IgE, IgG$_4$, or IgM is useful in determining the class or subclass of the antibodies of the circulating immune complex. The polyethylene glycol may range in molecular weight from 2,000 to 20,000, although 6,000 to 8,000 is preferred. A product for use in such an assay is a plate having wells or a test tube formed of plastic, polystyrene and polyvinyl chloride being preferred, with a layer of such non-proteinaceous, non-ionic layer on the plate wells or the cavity of the test tube. This product, if it is not to be used immediately, should be provided with a layer or film protecting the polymer layer from the air. The product may also be a solid non-proteinaceous, non-ionic plastic, capable of adsorbing immune complexes from a serium sample.

4 Claims, 4 Drawing Figures

ARTICLE FOR DETERMINING THE PRESENCE OF IMMUNE COMPLEXES

This application is a continuation-in-part of my application Ser. No. 363,967, filed Mar. 31, 1982, now U.S. Pat. No. 4,450,231.

This invention relates to a method of performing an immunoassay for the total quantity of circulating immune complexes, in a specimen of a serum or the like, and to determine the specific identity and quantity of antigen components thereof, and to determine the class or subclass of antibody components thereof, as well as to an article for use in performing such an assay and a method for making such article.

BACKGROUND OF THE INVENTION

All of the previously developed immuno assays in common use rely on a coating of a protein on a solid phase base, in order to react with immune complexes in the specimen of serum, spinal fluid, plasma, saliva, semen, tears, urine or the like. The presence of such immune complexes in such a specimen is indicative that a patient, from whom such a specimen was taken, has a condition such as rheumatoid arthritis, tumor, hepatitis, viral infection or the like. The ELISA test, described more particularly hereinafter, involves coating a solid phase base with a protein, washing with specified solutions, and placing the serum or other sample to be tested on the protein, to permit the protein to adsorb the immune complexes in the specimen. An enzyme labeled anti-species immunoglobulin, such as anti-human IgG coupled with an enzyme such as a phosphatase, is added and permitted to stand for a desired period of time, followed by washing preferably a number of times with a predetermined solution. Then a substrate is added, which will react with the enzyme then attached to the protein and normally change color, dependent on the amount of immune complex which has been bound. With a p-nitro phenyl phosphate, the color produced is yellow, but with other substrates, the color may be different. After a period of time, such as 30 minutes or more, the color change may be observed visually for a generally qualitative determination, although through the use of a spectrophotometer, a more accurate reading may be obtained than could be obtained visually.

Other in vitro assays for the detection of immune complexes include the Raji cell radio-immuno assay which measures (or quantitates) the amount of immune complexes through the use of a radioactive material such as an anti-IgG-$I^{125}$ labeled antiserum. After washing off the excess radiolabeled antiserum, the amount of immune complexes reactive with the radioactive material may be ascertained through use of a scintillation counter. The Raji cell radioimmuno assay test is described in *In Vitro Methods in Cell Mediated and Tumor Immunity* Section D, chapter 52 (Academic Press 1976, edited by Bloom, B. and J. David).

Previously developed isotype specificity tests, for the class or subclass of the antibody component of a circulating immune complex, utilizing a protein for initial reaction with a specimen, have been carried out but have not utilized a monomixture or an admixture of monoclonal or polyclonal anti-antibodies with a single or multiple immunoglobulin isotype, such as IgA, IgD, IgE, IgG, IgG4 or IgM. Determination of the antibody subclass sheds light on both the possible origin and the prognosis of the disease. However, no previous antigen specific assay, as to aid in the identification of circulating immune complex related diseases, such as rheumatoid arthritis, systemic lupus erythematosus, and the like, are known.

Since each of the previous tests require protein for initial reaction with a specimen, it is apparent that a much less expensive material to form a layer on a solid phase base would reduce quite materially the cost of the material used in the immunoassay and thus reduce the ultimate cost. In addition, the use of radioactive material ordinarily requires a special permit, and, more particularly, numerous precautions in handling and use. In addition, the radioactive material is quite expensive and hazardous.

One of the objects of this invention is to provide a novel method of performing an immunoassay of a specimen of body fluid or the like to determine the identity of an antigen of a circulating immune complex and the quantity of that complex; and to provide a novel method of performing an immunoassay of a specimen of a body fluid or the like to determine the class or subclass of an antibody of a circulating immune complex and the quantity of that complex; and to provide such methods which involve the use of a considerably less expensive material than the protein required for previous types of assays; and to provide such methods which will produce reliable and reproducible results; and to provide such methods which can be carried out with more ease and in a more simple manner than in similar tests; and to provide an article which is readily produced in quantity and which will reduce considerably the time involved in the actual assay; and to provide such an article which can be made so that it can be stored for long periods of time; and to provide a method of making such an article, by which the article can be made effectively and efficiently; and to provide such a method which can be carried out easily and effectively and at a significantly lower cost.

SUMMARY OF THE INVENTION

It has been discovered that polyethylene glycol and other material, such as polymeric polyols, or dextran or polyvinyl chloride or mixtures thereof, can attach to a solid phase base and also have the capability of adsorbing immune complexes which may be present in a specimen of human serum or the like and be effective to produce reliable immunoassay analyses for determining the quantity of circulatory immune complexes and can indicate the specific antibody chall or specific antigen component thereof. After the attachment of the polymer having such properties to the solid phase base, such as a microtiter plate, test tube or the like, the steps used in the assay method of this invention may be similar to the corresponding steps of the ELISA assay. However, the solid phase base must be one to which the polymer will attach and several plastic materials have been found to be the preferred material for the base, particularly polystyrene and polyvinyl chloride or any other material which will function in such a manner with the materials disclosed herein.

In one embodiment, the serum specimen can be reacted with the polymer, and then a radioactive material may be utilized as a label with any immunogloblen or anti-immunogloblen, such as an anti-human immunogloblin IgG which is tagged to a radioactive label such as Iodine 125 which in turn may be reacted with the immune complexes adsorbed by the polymer. Excess reactants may then be removed and the amount of radioactive material reacting with the adsorbed immune complexes measured, as by a scintillation counter, or the like, to achieve the assay for total circulating immune complexes or the class of the anti-body component thereof, or the specific antigen component thereof.

For the determination of the specific identity of the antigen component of a circulating immune complex, the steps of the ELISA assay may be followed, except that a monomixture or admixture of monoclonal or polyclonal antibodies with specificities for the antigens relevant to or specific for various circulating immune complex related diseases may be utilized. For instance, those having a specificity for native DNA may be used to identify systemic lupus erythematosus, while those having specificity to various joint components, such as collagen, elastin, and the like may be used to identify rheumatoid arthritis. Thus, enzyme conjugated monoclonal or polyclonal antibodies are substituted for the enzyme labeled anti-species immunoglobulin utilized in the ELISA assay for determining immune complexes.

For the determination of the isotype or antibody subclass of a circulating immune complex, the steps of the ELISA test may be followed, but utilizing the solid phase base of this invention and again monoclonal or polyclonal antibodies but conjugated with a single immunoglobulin isotype, such as IgA, IgD, IgE, IgG, IgG$_4$, or IgM.

The article of this invention, useful in each of the above immunoassay analyses, is a solid phase base having means for receiving a layer of the polymer and also a specimen to be tested, such as a series of wells in a planar surface of a titer plate or the cavity of a test tube, which is preferably formed of plastic, with such means having a coating or layer of a liquid phase, non-proteinaceous, non-ionic polymer having the capability of adsorbing immune complexes. The method of producing such an article can be the same as the first few steps of the assay method described previously. Also, the article is preferably protected by a layer of film which covers the polymer and specimen receiving means to delay evaporation of the layer of liquid phase material. The titer plate can also be made from a solid non-proteinaceous non-ionic polymer which is capable of being formed directly into a plate having the capability of adsorbing immune complexes as described herein.

DESCRIPTION OF THE PREFERRED EMBODIMENT

Figure 1:
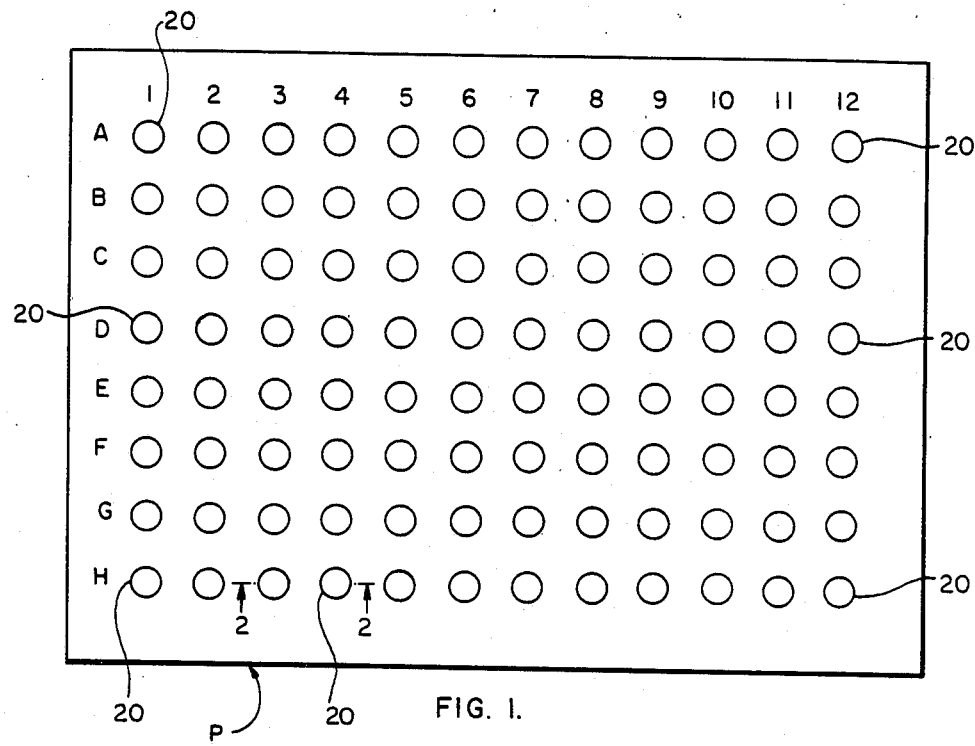
FIG. 1 is a top plan view of a plastic micro-titer plate which is adapted to form the article of this invention and is particularly useful in the immunoassay thereof.
Figure 3:
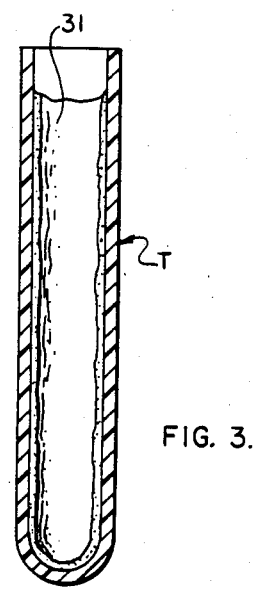
FIG. 3 is a longitudinal section, on an enlarged scale, of a test tube comprising another article useful in the immunoassay of the invention.

A solid phase base adapted to receive a test specimen, such as a microtiter plate P of FIG. 1, or test tube T of FIG. 3, or a polymer paper formed to provide wells or recesses, is treated in accordance with this invention for use in the detection of immune complexes, e.g. antigen-antibody complexes, such as are present in a human serum sample of a patient suffering from rheumatoid arthritis, tumor, hepatitis, viral infection or the like. Each of the plate P and test tube T are formed preferably of a suitable plastic, such as polystyrene or polyvinyl chloride. Plate P is provided with a series of wells 20, of a capacity as small as on the order of 0.2 cc, while the capacity of test tube T. may be on the order of about 5.0 cc. For testing, substantial number of specimens of body fluid, such as human serum, blood plasma, cerebral spinal fluid, or the like, together with a desired adequate number of controls, are placed in the wells 20 of the plate P. The wells of plate P may be provided in any suitable manner but are here divided into both horizontal and vertical rows, with suitable indicia systems to indicate each specific well. In the system shown in FIG. 1, the wells of the vertical rows may be idenfied by numbers, as from 1 through 12, while the wells of the horizontal rows may be identified by letters, as from A through H, to provide a more accurate correlation of the results with the samples being tested. As will be evident, there are 96 wells shown in FIG. 1, although the specific number may be varied as desired.

In accordance with this invention, a solution of non-proteinaceous, non-ionic organic polymer is used which is also capable of adsorbing immune complex, as well as wetting the plastic of plate P and test tube T. The preferred non-ionic polymer being polyethylene glycol, PEG, i.e. p-isooctyl phenyl ether or other compounds capable of functioning in a similar manner may be used. The PEG should range in molecular weight from about 2,000 to about 20,000 with a molecular weight of 6,000–8,000 preferred. A solution of PEG, having PEG concentration of about 5% to about 20%, with 9% being preferred, is poured or dipped onto plate P, or deposited in each well 20. After a sufficient period of time, preferably 12 to 24 hours, any excess PEG is shaken off the plate, leaving a layer 21 of FIG. 2, comprising PEG adhering to each well to the plate. A similar operation may be utilized in coating the inside of test tube T of FIG. 2 with a PEG layer 31, as by pouring the PEG solution into the test tube, letting it stand for a sufficient period of time, preferably for 12 to 24 hours, then shaking out the excess solution.

Figure 4:
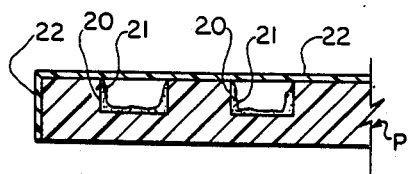
FIG. 4 is a cross section similar to FIG. 2 but taken at a position so as to include an edge of the titer plate of FIG. 1 and showing also a protective layer which prevents or delays the evaporation of a liquid polymer which is adhered to the wells of the titer plate.

It is also contemplated that polyethylene glycol polymers or adducts having a molecular weight of about 2000 to about 20,000 should be able to be used successfully in the present invention. Tests would indicate that polymeric materials having the proper wetting and reactivity characteristics should be suitable for use according to the present invention. The non-ionic polymer so deposited on the plate is preferably protected from the air, to prevent drying, as by a protective means such as the layer or film 22 of FIG. 4, since exposure to the air, as indicated in Example 3, for too long a time may result in the solvent evaporating, with the PEG becoming a powder and washing away when the serum is added, as described hereinafter.

Most preferably it is desirable to wash the PEG solution from the wells of plate P with a buffer solution before reacting the PEG with the immune complex containing serum. Typically, a carbonate-bicarbonate buffer solution may be utilized, at a pH of about 7.6, such as indicated by the following Table 1:

TABLE 1

| | |
|---|---|
| Na$_2$CO$_3$ | 1.5 g. |

TABLE 1-continued

| NaHCO$_3$ | 2.9 g. |
| H$_2$O | 1 liter |

Other buffer systems may be utilized, such as the phosphate buffer solution of Table 2, having a pH of about 7.4:

TABLE 2

| NaCl | 8 g. |
| KH$_2$PO$_4$ | 0.2 g. |
| Na$_2$HPO$_3$12H$_2$O | 2.9 g. |
| KCl | 0.2 g. |
| H$_2$O | 1 liter |

In each instance, an appropriate amount of PEG can also be added to the buffer solution. Also, if a non-buffered, aqueous solution of PEG has been added, a buffer solution may be added with the serum. It has been found that the titer plate, test tube or the like should be formed of plastic, since with other materials, the nonionic polymer useful in this invention may not produce adequate adherence to the substrate. A wide variety of materials may be employed if they exhibit the requisite characteristics for use in the method of this invention.

The application of the serum and the remainder of the assay may be conducted similarly to the standard ELISA assay described herein, in which a protein is utilized as the antigen, such as described in the 1979 book entitled *The Enzyme Linked Immunosorbent Assay (ELISA)* by Bidwell and Bartlett. FIG. 6 of this book is a chart of the indirect method for assay of antibody, which is described as being carried out as follows:

1. The relevant antigen is attached to the solid phase, then washed.
2. The diluted test serum is added, and incubated, followed by washing.
3. An enzyme-labeled anti-species-immunoglobulin is added and allowed to react, then washing is repeated. Unlabeled anti-species-immunoglobulin followed by labeled antigen to this second antibody can also be used.
4. The enzyme substrate is added. Degradation of substrate results in a color change. The amount and rate of color change is related to the amount of antibody in the test serum in step 2.

After the titer plate P has been treated to provide the PEG layer 21, an appropriate amount of the human serum to be tested or control serum or control solution, is placed in a well 20 of the titer plate, for instance, for adsorption by the PEG layer 21. For instance, 50 $\mu$l. of serum may be added to the appropriate well 20 by a calibrated pipetts, then left to stand, as at 37° C. for one hour or a longer time, as up to two hours, at a lesser temperature, such as from 37° C. down to 4° C.

Following the above, the layer 21, in which the immune complexes have been adsorbed, is washed, preferably three times, with a lightly saponified phosphate solution, such as the phosphate buffer solution of Table 2, to which has been added 0.5 ml. of "Tween 20", a standard detergent available from Sigma Chemical of St. Louis, Mo. Other equivalent detergents may, of course, be utilized. The preferable washing is for three times. Thus, one, two, three and four washings of different tests have indicated that three washings are desirable, but that the fourth appeared to produce no detectable improvement in the accuracy of the test.

Following washing, the comparative amount of immune complex bound to the PEG may be determined by the conventional radioactive method, such as involving the use of anti IgG-I$^{125}$, washing off excess of the latter and then measuring the amount of immune complex reactive by the use of a scintillation counter to determine the presence and amount of radioactive material. However, it has been discovered that the use of radioactive material may be dispensed with and the results procured more quickly, in comparison with previous tests involving the use of protein, by performing an enzyme linked immunosorbent assay, i.e. ELISA test, described at many places in the literature and specifically hereinbefore. As indicated, previous tests have used protein only for the determination of immune complexes and not a non-proteinaceous, non-ionic organic polymer. Thus, the present invention includes the addition of an anti-species immunoglobulin such as anti-human IgG coupled with an enzyme, a conventional product available from Sigma Chemical. After the enzyme has been added, the layer is permitted to stand, as at 37° C. for up to two hours, after which it is washed about four times with the phosphate buffer detergent solution of Table 2 or this phosphate buffer solution to which 9% of PEG has been added.

When the enzyme selected is a phosphatase, the substrate should preferably be p-nitro phenyl phosphate, and the concentration on the order of 1 mg. per ml., while 200 $\mu$l. of the substrate solution of Table 3, is then added to each well of the plate. When the enzyme selected is a peroxidase, the substrate can be phenylene diamine phosphate with a small amount of H$_2$O$_2$; when the enzyme selected is B-galactosidase, the substrate can be a galactoside; for other types of antibody coupled enzymes, an appropriate substrate should, of course, be utilized. The selection of a suitable substrate is within the purview of one skilled in the art of immunoassay works.

Following the above steps, the next reaction is with a color reagent, such as through the addition of a substrate specific for the enzyme which has been added to the solution of Table 3 at pH 9.8:

TABLE 3

| Diethanolamine | 10 g. |
| MgCl$_2$.6H$_2$O | 100 mg. |
| H$_2$O | 800 ml. |

The reaction with the color reagent, which takes place at room temperature, will produce a color change, if any is to be produced, within about 30 minutes. The reaction will produce a color change dependent upon the amount of immune complex bound to the plate. A color ranging from the absence of color to a very pale yellow represents less than a significant amount of immune complex. An intense yellow color can represent a fairly large amount of immune complex. A spectrophotomer, of the type usually utilized in ascertaining the results of an ELISA test, is generally more reliable than the human eye. Such a spectrophotomer, it is suggested, should be read at an absorbence of 405 nanometers for a phosphate washed substrate. Typically, such a substrate could produce a reading of less than 0.060 O.D. units when observing a normal serum. Conversely, a heat aggregated human gammaglobulin, heated to 63° C. for 30 minutes, has produced a reading of more than 0.060 O.D.

Determination of the precise identity of the antigen component of a circulating immune complex provides a valuable adjunct to the diagnosis of the causative condition or syndrome leading to the development of pathologic levels of a circulating immune complex and can provide the physician or veterinarian with valuable information pertaining to the actual etiology of the elevated circulating immune complex levels, as well as the prognosis of the disease itself. As described previously, a solid phase base having the means for receiving a coating layer of 9–10% polyethylene glycol, or other suitable polymer, and also a fluid specimen, i.e. a body fluid of mammalian or avian origin or the like, may be used to facilitate qualitative or quantitative assessment of the circulating immune complex. This test differs from the earlier description by the use of either an admixture or a monomixture of monoclonal or polyclonal antibodies with specificities for the antigens relevant to or specific for various circulating immune complex related diseases. Thus, those antibody reagents used to aid in the identification of the antigen component of systemic lupus erythematosus have a specificity for native DNA, while those antibody reagents used to aid in the identification of rheumatoid arthritis have a specificity to various joint components, such as colloagen, elastin, and the like. It should be noted that this is intended to be used as a separate immunoassay following the initial usage of the antibody isotype specificity test described below. The ability to determine the precise nature of the antigen component of the circulating immune complex is an extremely important and desirable characteristic for a circulating immune complex assay. For such a test, a solid phase, plastic base adapted to receive a test specimen, such as a test tube, microtiter plate, polymer paper, disc or card having wells or recesses, is utilized. The solid phase base is formed of a suitable polymer, preferably of a polymer such as polystyrene or polyvinyl chloride. For testing a substantial number of specimens, a 96-well microtiter plate, a 50-well cuvette-cassette or other similarly configured solid phase base may be employed, such that horizontal and vertical rows of wells, with suitable indicia systems, are capable of identifying each individual specimen.

As also described previously, a solution of a non-proteinaceous, non-ionic organic polymer which is also capable of adsorbing immune complexes, as well as coating the solid phase base, is utilized, with the preferred non-ionic polymer being polyethylene glycol or PEG. The PEG used may range in molecular weight from about 20,000 with a preferred range in molecular weight of 6000–8000. A solution of PEG having a preferred concentration of 9–10% is introduced into each well of the solid phase base. After an incubation period of less than 12 hours at 4° C., excess PEG solution is decanted from the solid phase base, leaving a coating layer of PEG adhering to the walls of each well contained within the solid phase base. The solid phase base containing PEG may be stored at 4° C. for up to 60 days, if appropriately sealed.

Following the removal of excess PEG from the solid phase base, it is desireable to wash the wells with a buffer solution before reacting the PEG coating with body fluids containing circulating immune complex. Typically, a phosphate buffered saline solution may be utilized, as at a pH of 7.4 to 7.6, such as indicated by Table 1 or Table 2, shown previously.

Samples of human body fluid, such as plasma, serum, tears, saliva, semen, urine, peritoneal aspirates, intestinal aspirates, lung aspirates or cerebral spinal fluid, from patients suffering from or suspected to be suffering from rheumatoid arthritis, systemic lupus erythematosus or various other circulating immune complex related diseases, as well as control samples, are added to the PEG treated base, such as 25 $\mu$l. by a calibrated pipette to the appropriate wells 20 of plate P. Each sample coats and becomes attached to the PEG of the base, which is then washed three times, as with the phosphate buffer solution of Table 2 to which has been added "Tween 20", as described previously. Following washing, the samples are incubated for about 1.5 hours at 37° C., followed by washing three times with the phosphate buffer solution of Table 2 to which "Tween 20" has been added, as described previously. Then, a diluted enzyme conjugated admixture of either monoclonal or polyclonal antibodies, having the appropriate antigen specificity, as described above, are introduced into each well of the solid phase base, and allowed to incubate for up to 45 minutes at 37° C. Examples of available monoclonal antibodies useful in the present invention for determination of antigen specificity include Anti-Leu 1, Anti-Leu 2, Anti-Leu 3, Anti-Leu 4, Anti-Leu 5, Anti-Leu 7, Anti-Leu 10, Anti-Leu 11, and Anti-Leu 12, as well as Anti-Leu M1, Anti-Leu M2, Anti HLA DR, Anti Leucocyte and Anti IgG.

Following a wash with the buffer of Table 1 three times, 50 $\mu$l. of the appropriate enzyme substrate is introduced into each well of the solid phase base. The enzyme substrate reaction is allowed to occur, during which degradation of the substrate results in a color change. This reaction is allowed to take place at room temperature for less than 20 minutes. Many enzyme systems lend themselves to this application, such as peroxidase, phosphatase or B-galactosidase, as described previously.

Following the completion of the enzyme substrate incubation, 50 $\mu$l. of a 2.5M $H_2SO_4$ stopping solution is introduced into each well of the solid phase base. This solution simply halts the enzyme substrate reaction and therefore stabilizes the color changes that have occured during the same. At this time, the color changes that have occurred within the wells of the solid phase base can be measured either visually or spectrophotometrically. Values obtained for unknown specimens should be compared to standards of known antigen specificity, so that precise antigen characterization of unknown specimens can be assigned to unknown specimens. Although an assay of human specimens has been descibed above, it should be pointed out that such assay should be equally operative for body fluids from other mammals or avians.

Determination of the isotype (antibody class and/or subclass) specificity of the antibody component of a circulating immune complex, tends to shed light on both the origins and prognosis of the disease and is helpful in conjunction with the determination of the precise identity of the antigen component of the circulating immune complex, both that determination and the present determination being helpful in conjunction with the determination of the amount of immune complexes. As before, a solid phase base adapted to receive a test specimen, such as a test tube, microtiter plate, disc or card is treated in accordance with this invention for use in the quantitative assessment of the level and antibody class or subclass of circulating immune complexes, such as are present in a sample of human body fluid from patients suffering or suspected of suffering from rheumatoid arthritis, systemic lupus erythematosus, or other circulating immune complex related diseases. A solid phase base, as described previously, is utilized. The steps of this assay may be essentially the same as described above in connection with the determination of the precise identity of the antigen component of the immune complex, except for the use of an enzyme labeled, isotype specific, anti-species conjugate. Such conjugates are monoclonal or polyclonal antibodies to immunoglobulin specific to a class, such as anti-human IgE, anti-human IgG, anti-human IgA, anti-human IgD, anti-human IgG4 or anti-human IgM, each tagged with an appropriate enzyme. The diluted conjugate, for example, 1:1000, is added to the wells in which the specimens have been adsorbed by the polymer on the base, such as 25 μl to each well, and allowed to react for 30 minutes during incubation at 37° C.

Following a three times buffer wash to rid the wells of excess anti-species conjugate, 50 μl of the enzyme substrate is introduced into each well of the solid phase base. The enzyme substrate reaction is allowed to occur during which the degradation of substrate results in a color change. For a peroxidase O-phenylenediamine enzyme substrate system, the working substrate is composed of constituents as below.

TABLE 4

| Phosphate buffered saline | 25.00 ml |
|---|---|
| O—phenylenediamine | 10.00 mg |
| 30% hydrogen peroxide | 8.25 ul |

The use of isotype specific anti-species conjugates can also be combined with any suitable enzyme system, such as the B-galactosidase or the phosphatase enzyme systems.

Following an enzyme-substrate reaction time of approximately 20 minutes, a 2.5M Hhd 2SO$_4$ stopping solution is introduced into each of the wells of the solid phase base. Then, the relative color change that has occurred within each of the wells of the solid phase base can be measured, either visually or spectrophotometrically.

Commercially available polyethylene glycol or PEG (as that term is understood) can conceivably be more effective than a non-ionic organic polymer which is potentially reactable or physically compatible with both the plate P or test tube T and the immune complexes, such as dextran or polyvinyl chloride, since the latter is less effective and less selective than polyethylene glycol. It is theorized, though not definitively determined, that the interaction with immune complexes may be due to stearic exclusion of the complexes from the domain of the PEG based on immuno-precipitation characteristics of the PEG as suggested by Rampling, M. W. *Biochemical Journal* (1974). The present discovery is unexpected because the polymer is immobile on a solid phase base, rather than mobile in the solution, as reported; so that the theory of stearic hindrance does not appear to explain the results observed herein. In any event, the use of PEG or any other polymer of this invention has not been suggested or tried for adsorption of an immune complex onto a solid phase base as prepared herein.

In addition to reacting the polymer with the solid phase base, then adding the serum, it also appears possible to mix the polymer with the serum and simultaneously deposit the polymer on the solid phase base for reaction with both the base and the serum. The addition of a buffer to the solution, as of Table 1 or Table 2, also appears desirable, with the remainder of the steps, including washing and testing, proceeding as before.

Further, the formation and measurement of immune complexes formed in vitro may be utilized, according to the present invention, to determine the probable presence or absence of a predetermined suspected condition of the patient. A sample of the same serum which is also tested without such reaction, can be reacted in a test tube with the suspected antigen, which may result in the formation of immune complexes. For instance, in order to test for hepatitis antibody, a sample of the serum may be reacted in a test tube with hepatitis virus, such as for one hour at 37° C., accompanied by gentle shaking. The resultant will be used as one sample in a test of this invention, with another sample being serum which has not been reacted with the virus. Then if the sample which has been reacted with hepatitis virus produces a high reading, with respect to the presence of immune complexes, while the normal serum produces a much lower reading but shows the presence of immune complexes, this result will be an indication that the antibodies which are specific for hepatitis are produced as a result of the presence of immune complexes. To test for the presence of a condition due to any other particular disease, a bacteria productive of that disease can be reacted with a sample of the serum and a comparison of the results of the test of such reacted serum, with the test of the normal serum, is an indication of whether the presence of immune complexes is due to such bacteria. For a test to indicate the presence or absence of rheumatoid arthritis, a sample of the serum from a patient can be reacted with human immunoglobulin G (IgG), which will act as an antigen to form immune complexes. When the sample so reacted is tested along with a normal sample of the serum, a comparatively high reading for the sample reacted with the IgG and a considerably lower reading for the normal (unreacted) sample will be an indication that the presence of the immune complexes has been produced by antibody to IgG. In a similar manner, DNA may be added to a serum sample in order to determine the presence or absence of systemic lupus erythematosus, i.e. SLE. Similar indication with respect to other suspected conditions can be obtained by adding an appropriate virus, bacteria, or other antigens to one serum sample and simultaneously testing a normal (unreacted) serum sample.

The efficacy of the solid phase base reacted with the polymer and the testing of serum for one class of immune complexes has been demonstrated by the following examples.

EXAMPLE 1

A titer plate corresponding to plate P of FIG. 1 was used. A carbonate-bicarbonate buffer solution of Table 1, containing 9% PEG having a molecular weight of about 6000, was added to the wells 20, the plate allowed to stand for 12 hours at 37° C., then the excess solution shaken off to provide the layers 21 of FIG. 2 in the wells 20. Then, duplicate samples of human serum obtained from various patients of a hospital were placed in 72 of the 96 wells of the plate. In addition, negative controls of serum from babies who presumably had no immune complexes were placed in 21 of the wells, while 4 positive controls, consisting of serum from patients who had been clinically diagnosed as having rheumatoid arthritis, were placed in four of the wells. Also, a control to test the function of the substrate, consisting of anti-human IgG antigen labeled with a phosphatase enzyme, was placed in one well. After addition of the serum and sample, the plate was left standing for one hour at 37° C. to permit the immune complexes, if any, of the serum specimens to react with the PEG layers. Then, the wells were each washed three times with the phosphate buffer solution of Table 2 to which had been added 0.5 ml. of "Tween 20" detergent.

Following washing, an anti-human IgG immunoglobulin labeled with a phosphatase enzyme was added to the wells and allowed to incubate for two (2) hours at 37° C. After incubation, the excess antisera was removed and the plate was washed three (3) times with the phosphate buffer solution of Table 2 containing "Tween 20" detergent.

Following washing, a diethanolamine solution of Table 3 to which p-nitro phenyl phosphate had been added, as described previously, was added to each well and the reaction, if any, permitted to take place. After 30 minutes at 37° C., the color of the reacted layers in the respective wells was measured with a spectrophotomer, read at an absorbence of 405 nanometers. As expected, the well containing the substrate function test i.e. enzyme labeled antihuman IgG antiserum had a reading of 2.0 while 20 of the 21 assumed normal samples or negative controls read from 0.001 to 0.07 and two read 0.000, while one assumed normal sample read 0.793, which was suggestive of an immune complex type disorder. The remaining test readings ranged from 0.02 to 0.575, with the differences for duplicate specimens, approximating the differences for duplicate specimens, within the inventor's experience relating to the use of a protein coating on a solid phase, plastic base and an ELISA assay or a Raji cell radio immunoassay. It was thus concluded that the above test equaled the reliability of the radio immunoassay and the ELISA assay, each using protein as the layer reacting with plastic.

EXAMPLE 2

Figure 2:
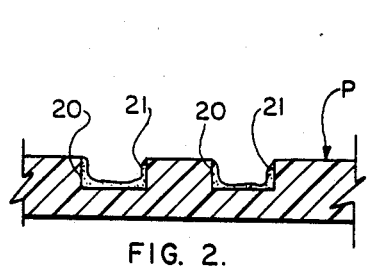
FIG. 2 is a fragmentary cross section, taken along line 2—2 of FIG. 1 on an enlarged scale, showing the microtiter plate prepared for use.

A titer plate corresponding to plate P of FIG. 1, was treated in the same manner as in Example 1, to produce the PEG layers 21 of FIG. 2. Then, 32 human serum specimens obtained from a hospital were placed in 64 wells of the titer plate, i.e. with a duplicate of each specimen. Nine negative controls, two positive controls and one substrate control were also utilized. The same procedures as in Example 1 were followed, with testing of the color produced in the same manner.

All of the negative controls produced a reading of 0.00, while the two positive controls produced readings of 0.78 and 0.62, respectively, and the substrate control produced an intense yellow color and a reading of 0.8881. The highest reading, other than the controls, was 0.739 for a patient who was actually quite ill. Thirty-five of the samples produced readings of less than 0.060, the number being accounted for by the fact that duplicate specimens produced one reading of less than 0.060 and the other slightly higher than 0.060. Of the remaining readings, eight were between 0.060 and 0.100, seven were between 0.101 and 0.200, three were between 0.201 and 0.300, two were between 0.301 and 0.400, while two duplicate readings were above 0.401, i.e. 0.519 and 0.737, as noted above. Again, the variance in the readings of duplicate specimens approximated the experience of the inventor with respect to readings produced by duplicate specimens when using a protein on a solid phase, plastic base and an ELISA assay or a Raji cell radio immunoassay.

The following example shows the necessity for maintaining the liquid or wet condition of the polymer.

EXAMPLE 3

A titer plate corresponding to plate P of FIG. 1 was treated in the same manner as in Example 1, to produce the PEG layers 21 of FIG. 2. The plate was allowed to stand unprotected for four days at 37° C. When the plate was then desired to be used for testing samples of heat aggregated human gamma globulin, it was found that the buffer solution had evaporated, leaving a layer of powder on the plate, apparently PEG. Much of this powder washed away when a test solution was placed in a well, showing that any serum added to the wells would wash away the powder and that the plate was not usable for any further steps in the test.

The following examples, carried out prior to Example 1 and 2, show the comparative results of tests in accordance with this invention, using heat aggregated human gamma globulin, utilized as positive controls in Examples 1 and 2.

EXAMPLE 4

A titer plate corresponding to plate P of FIG. 1 was treated in the same manner as in Example 1, to produce the PEG layers of FIG. 2, while human serum was heated at 63° C. for 30 minutes, to provide heat aggregated human gamma globulin. The plate was washed with the solution of Table 2 to which 0.5 ml. of "Tween 20" had been added. Two wells 20 of FIG. 2 were filled with the heat aggregated gamma globulin, diluted with water in a 1:4 ratio, while a 1:4 solution of the wash solution was added to two other wells. The plate was shaken occasionally but maintained at 37° C., then washed twice with the wash solution as previously used. To each of the four wells was added a 1:200 dilution of anti-human IgG coupled with phosphatase enzyme, then permitted to incubate for one hour. The plate was then washed twice with the same wash solution and a p-nitro phenyl phosphate substrate in the amount of 1 mg. per ml. in the substrate solution of Table 3 was added. After 40 minutes, the wells were examined by eye and it was found that the wells containing the wash solution were both clear and without color, whereas the wells initially containing the human gamma globulin were clear but an intense yellow in color.

EXAMPLE 5

A titer plate corresponding to plate P of FIG. 1 was treated in the same manner as in Example 1 to produce PEG layers 21 of FIG. 2, while a human serum was heated as in Example 4 to produce human gamma globulin. Various specimens were made at increasing dilutions, as in Table 4 below, and the test proceeded as in Example 4, except that the color of the substrate was measured by a photospectrometer as in Examples 1 and 2. The readings obtained, at an absorbence of 405 nanometers, are set forth below in Table 5.

TABLE 5

| Dilution | Reading of photospectrometer |
|---|---|
| 1:8 | 0.360 |
| 1:16 | 0.299 |
| 1:32 | 0.192 |
| 1:64 | 0.101 |
| 1:128 | 0.048 |
| 1:256 | 0.006 |
| 1:512 | 0.000 |
| 1:1024 | 0.000 |

When the above readings were plotted on a graph, with the decimal readings plotted as ordinates and the dilution factors plotted as abscissa on a geometric basis, i.e. with the successive dilutions indicated above spaced apart equally, a straight line was formed by the points for the 1:8 through the 1:128 dilutions. The readings for the 1:256 dilution was above the slope of the straight line, if extended, while the 1:512 and 1:1024 readings were on the abscissa axis. Since such a straight line is typical of reliable ELISA tests, it was considered that the reliability of the present test had been demonstrated.

EXAMPLE 6

The wells of a titer plate, corresponding to plate P, were coated with a 9% solution of PEG having a molecular weight of 6000, and then washed, as in Example 5. One series of samples was prepared from heat aggregated gamma globulin, produced as in Example 4, and aqueous solutions of various dilution were prepared therefrom with the dilution of Table 4 above. To test the sensitivity of the procedure, human serum was repeatedly frozen and thawed, to produce aggregated gamma globulin and a second series of samples were similarly diluted in aqueous solution, as in Table 5. Then 200 µl of each sample were added to a well of the plate and 90 minutes at room temperature allowed for incubation. The plate was then washed two times with the solution of Table 2 to which 0.5 ml. of "Tween 20" had been added. Then, 200 µl. of anti-human IgG coupled with phosphatase enzyme and diluted 1:500 was added to each well and permitted to incubate for 90 minutes, then washed two times with the above washing solution. A substrate was added to each well, i.e. 200 µl. of p-nitro phenyl phosphate in the substrate solution of Table 3 permitted to react for 40 minutes and then quenched, with a 3N NaOH solution.

The following Table 6 shows the results of observation by the eye which, although not as accurate as readings by a photospectrometer, were sufficient to show the sensitivity of the test.

TABLE 6

| Dilution Proportion | Heat Aggregation Sample | Freeze and Thaw Specimens |
| --- | --- | --- |
| 1:8 | ++ | ++ |
| 1:16 | ++ | ++ |
| 1:64 | ++ | ++ |
| 1:128 | ++ | +/− |
| 1:512 | +/− | − |
| 1:1024 | +/− | − |
| 1:2048 | − | − |

Where:
++ indicates strong color
+/− weak color
− clear solution, with no yellow The following example was an experiment to compare polyethylene glycol having a molecular weight of 20,000 with that having a molecular weight of 6,000:

EXAMPLE 7

A 10% solution of PEG having a molecular weight of 20,000 was used to coat one plate corresponding to plate P of FIG. 1 and a 10% solution of PEG of 6,000 molecular weight was used to coat an identical plate. Each plate was washed with the phosphate solution of Table 2 to which "Tween 20" had been added, as before. Normal human serum was heated as in Example 4, but excess serum was centrifuged off and the remainder made into duplicate samples having the dilutions set forth in Table 7 below. Samples of the various dilutions were added to each plate and left at room temperature for 3½ hours, accompanied by shaking and followed by washing two times with the saponified phosphate solution. A 1:200 solution of antihuman IgG coupled with an enzyme was added to each well and the plates shaken in a micro-mixer for between 10 and 15 minutes, then allowed to incubate at 37° C. for 30 minutes and at room temperature for 1½ hours. Each plate was then washed with the lightly saponified phosphate solution and 200 µl. of p-nitro phenyl phosphate substrate, as in Example 4, was added to each well. After 20 minutes, the wells containing samples were examined visually, with the results indicated in Table 7.

TABLE 7

| Dilution Proportion | Layer of PEG 6000 | Layer of PEG 20,000 |
| --- | --- | --- |
| 1:8 | ++ | − |
| 1:16 | ++ | +/− |
| 1:32 | ++ | +/− |
| 1:64 | ++ | +/− |
| 1:128 | ++ | + |
| 1:256 | +++ | +/− |
| 1:512 | ++ | +/− |
| 1:1024 | +++ | − |
| 1:2048 | − | − |
| 1:4096 | − | − |

Where:
+++ indicated greatest intensity
++ indicated strong color
+/− indicated weak color
− indicated clear solution, no color From the above test, it was concluded that the PEG 6000 appeared to react with the immune complexes more effectively.

It will be understood that other embodiments of this invention, other than those described or indicated, may be utilized and that various changes may be made without departing from the spirit and scope of this invention. For example, the tests described herein can be designed to detect a depressed level of circulating immune complexes as evidenced by a color change less than a color change evident in a normal circulating immune complex level. This may be an indication of immunosuppression, either due to a pathological immunosuppression disease such as Acquired Immune Deficiency Syndrome (A.I.D.S.) or others, or induced by drug therapy, either accidentally or otherwise, such as the use of immunosuppressive drugs, such as cyclosporin-A, used in organ transplantation surgery.

Therefore, the scope of the present invention is intended to be limited only by the prior art as applied to the claims.

What is claimed is:

1. An article for use in performing an immunoassay on a specimen to determine the presence or composition of immune complexes, comprising:
   a solid phase base containing a surface capable of receiving a coating layer thereon; and
   a coating layer received on said surface, said layer consisting of a non-proteinaceous, non-ionic polymer selected from the group consisting of polyethylene glycol, dextran, polyvinyl chloride, and mixtures thereof, which is adhered to said surface and capable of absorbing immune complexes which may be present in fluid specimens contacted with said surface.

2. An article as defined in claim 1, wherein said non-ionic polymer is propylene glycol having a molecular weight from about 2,000 to about 20,000.

3. An aticle as defined in claim 1 wherein said polymer is a polymeric polyol.

4. An article as defined in claim 1 wherein said solid phase base is a plastic tube having a hollow interior.

* * * * *